United States Patent [19]

Strentz

[11] Patent Number: 4,710,701
[45] Date of Patent: Dec. 1, 1987

[54] CAPACITIVE CELL FOR CONTINUOUS MEASUREMENT OF THE LINEAR MASS OF TEXTILE PRODUCTS

[75] Inventor: Daniel Strentz, Mulhouse, France

[73] Assignee: Superba S.A., Mulhouse, France

[21] Appl. No.: 879,136

[22] Filed: Jun. 26, 1986

[30] Foreign Application Priority Data

Sep. 24, 1985 [FR] France ............................. 85 14234

[51] Int. Cl.$^4$ ...................... G01R 27/26; B65H 63/06
[52] U.S. Cl. .................................... 324/61 P; 28/227; 73/160
[58] Field of Search ............... 324/61 R, 61 P, 60 R, 324/60 C; 28/227; 19/0.2, 0.23, 0.25; 200/61.13, 61.16, 61.18; 340/677; 66/163, 158, 157; 318/662, 652; 73/159, 160

[56] References Cited

U.S. PATENT DOCUMENTS

| Re 23,368 | 5/1951 | Grob et al. ...................... 324/61 R |
| 2,950,436 | 8/1960 | Butticaz et al. ................. 324/61 R |
| 3,009,101 | 11/1961 | Locher ............................ 324/61 P |
| 3,313,991 | 4/1967 | Kelsey et al. ................... 324/61 R |
| 3,879,660 | 4/1975 | Piso ................................ 324/61 R |

Primary Examiner—Reinhard J. Eisenzopf
Assistant Examiner—Jack B. Harvey
Attorney, Agent, or Firm—Erwin S. Teltscher

[57] ABSTRACT

Device comprising two identical air capacitors for continuous measurement of the linear mass of textile products. The thread is passed through the air gap of one of the capacitors. Its presence causes differences in capacitance between the two capacitors which are used to detect any irregularities in the thread. The device is characterized in that it comprises a means of simultaneously modifying the air gap of both capacitors to enable different grades of material to be monitored.

5 Claims, 3 Drawing Figures

CAPACITIVE CELL FOR CONTINUOUS MEASUREMENT OF THE LINEAR MASS OF TEXTILE PRODUCTS

BACKGROUND OF THE INVENTION

This invention concerns a device designed for continuous measurement of variations in the linear mass of textile products such as thread, wicks, ribbon etc.

This type of device is already known in principle for the detection of variations in cross-section, or the presence of areas of greater thickness in threads, in view of eliminating them. It basically consists of passing the product between the two plates of an air capacitor, using as a basis for measurement the variations in its capacitance in terms of the cross-section of the product. These variations are compared to the fixed capacitance of a reference capacitor. They are then amplified and processed by a micro-computer as shown in FIGS. 4 and 5 of the applicant's French Pat. No. 83/10360.

One disadvantage of this device is the need, due to the fact that the variations are very small, for very highly mechanically and electrically stable measurement electrodes forming part of the capacitor plates. In the case of threads of very differing grades, the use of pairs of electrodes has been proposed that are separated by equally different spaces. The device then comprises, as shown in FIGS. 2 and 3 of the French Pat. No. 71/24828, a number of fixed pairs of electrodes selected according to the different products to be tested or according to the different grades of a single product.

The variations in capacitance between each pair of electrodes, which are due to the variations in the dielectric constant of the thread passing between them, are transformed into electrical signals by connecting the capacitor to a resonant circuit, whose variations in frequency of resonance can be monitored.

The inherent difficulty in this system is the problem of introducing and extracting each product into and from the appropriate test corridor and this represents a certain limitation in use as well as a possible cause of error. In addition, the juxtaposition of the electrodes can cause interactions with a detrimental effect on the quality of the measurement.

SUMMARY OF THE INVENTION

The device according to the invention solves this problem in that it comprises a single pair of capacitors, i.e.: the measurement capacitor and reference capacitor, and means for modifying the air gap of each of them simultaneously in terms of the thread to be tested.

The device according to the invention also comprises a means for eliminating any interaction between the capacitors as well as a means for rapid introduction and extraction of the threads.

The improved device not only enables the detection of irregularities in the product but also their eventual frequency of occurrence, their location and their origin in view of eliminating them.

The device is comprised of two fixed core frames and two mobile core frames mounted on two mobile blocks driven by two motors so as to maintain the same air gap between each mobile and fixed core frame. This air gap is determined by the optimal amplitude signal obtained in terms of the thread grade.

Each of the two capacitors formed by the mobile core frame/block is shielded.

Movement of each mobile block is determined by transmission of the rotation of the motor, for example a step motor excited in one direction or the other depending on the signal obtained by comparison of the capacitances of the measurement and reference capacitors. This signal is received in a central unit which controls the whole of the system, i.e.: feeds back to the motors the order for excitation until the optimum air gap is reached and trips the electrovalves controlling the thread extraction jacks and other programmed functions.

DETAILED DESCRIPTION OF THE DRAWINGS

The different details in the construction of the device shall now be described with reference to the appended drawings in which.

DESCRIPTION OF THE PREFERRED EMBODIMENT

Figure 2:
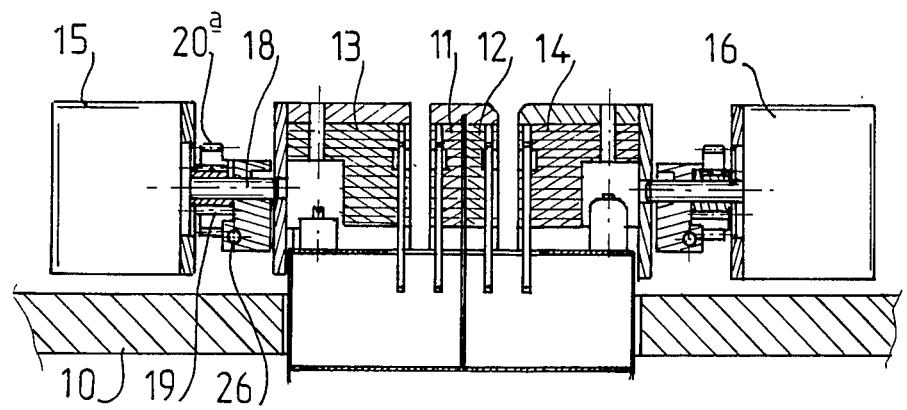
FIG. 2 is a lengthwise view along line II—II of FIG. 1.
Figure 1:
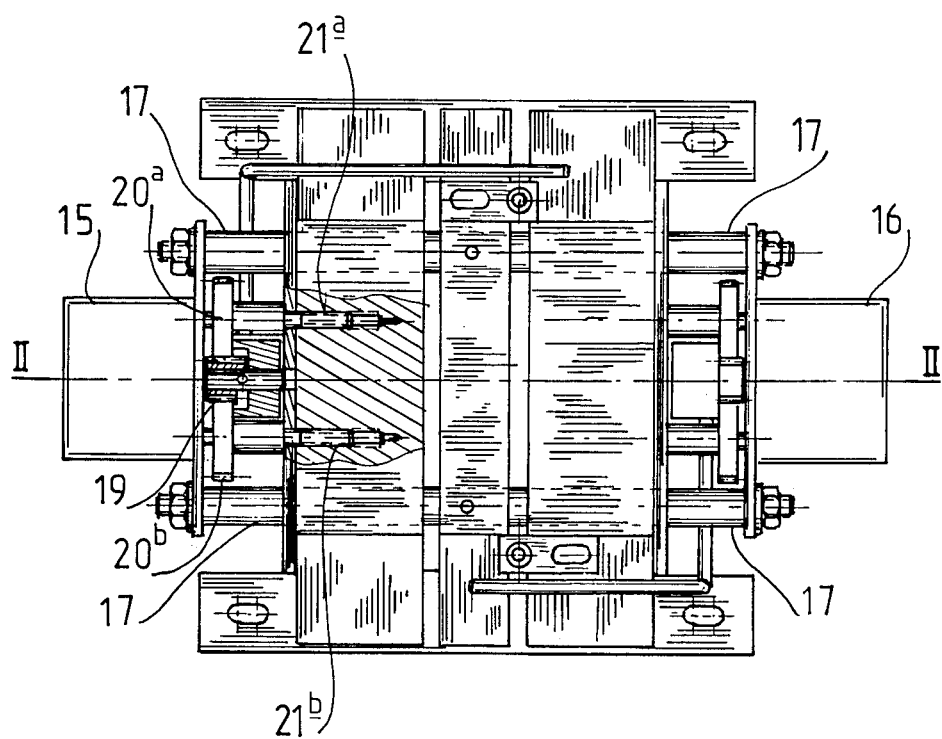
FIG. 1 is a front view of the device without the associated electronics.

According to the invention, and as shown in FIGS. 1 and 2, the sensor mounted on a fixed structure 10 comprises two fixed core frames 11 and 12 and two core frames 13 and 14 mounted on blocks and sliding on guide pins 17. These pins are driven by two step motors 15 and 16 by way of a transmission system which will now be described in more detail.

The exit shaft 18 from each motor is fitted with a pinion 19 which connects with two cogs 20a and 20b, which are themselves coaxial to two screws 21a and 21b interacting with the threads bored in the corresponding block. In this way, rotation in one direction or the other of motor 15 (or 16) causes block 13 (or 14) to move away from or nearer to its associated fixed core frame 11 (or 12).

Obviously, instead of a fixed and a mobile core frame, two mobile blocks could also be used and each motor would then drive a pair of pins each comprising two inversely oriented threads and each operating with one of the blocks.

Figure 3:
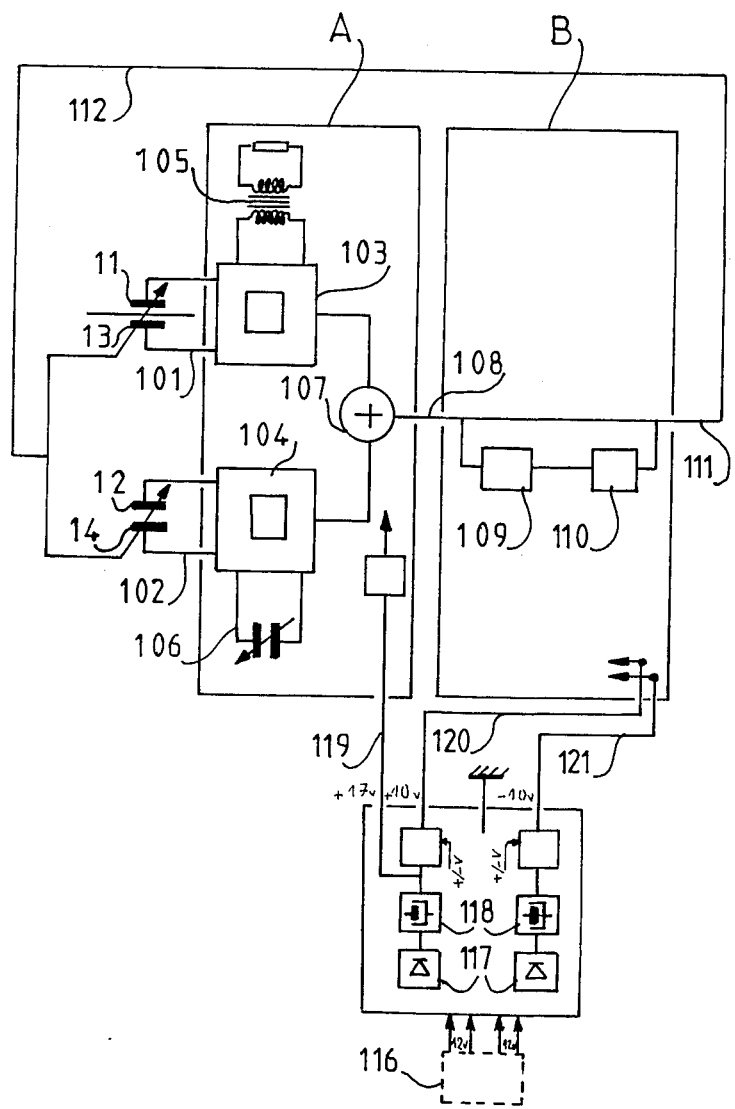
FIG. 3 is a block diagram of the electronics associated with the device as represented in FIGS. 1 and 2.

FIG. 3 shows a block diagram of the electronics associated with capacitors 101 and 102, which are formed respectively by core frames 11/13 and 12/14. With the thread to be tested passing between, for example, frames 11/13, capacitor 101 is the measurement capacitor with 102 considered as the compensating capacitor. Frames 11/13 are connected to an oscillator circuit 103 associated with an approximate adjusting circuit 105. Core frames 12/14 are connected to an oscillator circuit 104 thus enabling fine adjustment by capacitance 106. The exits from oscillators 103/106 are connected to a mixer 107 to obtain a frequency signal 108 characteristic of the variations in capacitance arising in 101 during passage of the thread.

This signal 108, emitted by the oscillator/mixer unit A, is then transmitted to unit B where, after any necessary shaping in circuit 109, it passes into a frequency/voltage converter 110.

Units A and B are supplied from a transformer 116 (220/2×12 V) whose output, after rectifiers 117 and filters 118, supplies via 119 the oscillator/mixer block A with 17 V and via 120–121 the converter block B with +10 V/−10 V.

The signal 111 obtained on exit from unit B is then transmitted, after any necessary appropriate filtering, to a microprocessor (not shown).

Examination of the signal obtained in this processing unit indicates whether the value of the selected air gap is optimum for the thread under test. If this is not the case, the data collected enables this value to be modified accordingly to exciting the motors and thus modifying the air gaps until the optimum value is reached.

It is this feedback process which is represented by connection 112 in the form of a means of adjusting the capacitors 101–102 according to signal 111.

This re-balancing used to be carried out by measuring the grade and the type of thread under test.

The device has an additional advantage in that it enables the exit voltage to be determined before and after measurement. Effectively, this enables variation of the oscillator to be determined and in the event of it being linear, which is most probable, enables it to be taken into account for further calculations. It is in this way that the invention enables localisation and rectification of faults in a thread.

I claim:

1. Device having two identical air capacitors for continuous measurement of a linear mass of textile products, wherein a thread is passed through an air gap of one of the capacitors, and wherein said thread's presence causes differences in capacitance between the two capacitors which are used to detect any irregularities in the thread, comprising means of simultaneously modifying the air gap of both capacitors to enable different grades of material to be monitored.

2. Device according to claim 1, characterized in that it comprises two fixed core frames and two mobile core frames, the latter being driven by two motors, preferably, so as to obtain between each corresponding mobile and fixed core frame an optimum air gap determined at a start of measurement in terms of a signal amplitude.

3. Device according to claim 2, characterized in that the fixed core frames are placed side by side in the center of the device and the two mobile core frames are each mounted with a motor and a clutch on respective ends of the device.

4. Device according to claim 2, characterized in that movement of the two mobile frames is determined by rotation of screws in threaded housings in the respective frames, and wherein said screws are driven by the motors by way of step down gear systems.

5. Device according to claim 1, characterized in that the capacitors are shielded.

* * * * *